(12) United States Patent
Acher et al.

(10) Patent No.: US 9,638,635 B2
(45) Date of Patent: May 2, 2017

(54) SPECTROMETER FOR ANALYSING THE SPECTRUM OF A LIGHT BEAM

(71) Applicant: HORIBA JOBIN YVON SAS, Longjumeau (FR)

(72) Inventors: Olivier Acher, Gif sur Yvette (FR); Simon Richard, Villebon sur Yvette (FR); Christian Brach, Saint Arnoult en Yvelines (FR); Viviane Millet, Linas (FR); Sebastien Corde, Paris (FR); Daphne Heran, Montrouge (FR)

(73) Assignee: HORIBA JOBIN YVON SAS, Longjumeau (FR)

( * ) Notice: Subject to any disclaimer, the term of this patent is extended or adjusted under 35 U.S.C. 154(b) by 0 days.

(21) Appl. No.: 14/649,096

(22) PCT Filed: Nov. 29, 2013

(86) PCT No.: PCT/FR2013/052900
§ 371 (c)(1),
(2) Date: Jun. 2, 2015

(87) PCT Pub. No.: WO2014/087081
PCT Pub. Date: Jun. 12, 2014

(65) Prior Publication Data
US 2015/0316476 A1 Nov. 5, 2015

(30) Foreign Application Priority Data

Dec. 4, 2012 (FR) ...................................... 12 61625

(51) Int. Cl.
*G01J 3/447* (2006.01)
*G01N 21/64* (2006.01)
(Continued)

(52) U.S. Cl.
CPC ............ *G01N 21/645* (2013.01); *G01J 3/021* (2013.01); *G01J 3/0224* (2013.01); *G01J 3/18* (2013.01);
(Continued)

(58) Field of Classification Search
CPC G01J 3/02; G01J 3/0224; G01J 3/447; G01N 21/645
See application file for complete search history.

(56) References Cited

U.S. PATENT DOCUMENTS

| 5,657,121 A | 8/1997 | Nishina | |
| 7,352,459 B2 * | 4/2008 | Gould | G01J 3/02 250/458.1 |

(Continued)

FOREIGN PATENT DOCUMENTS

| DE | 195 39 004 A1 | 4/1996 |
| DE | 10 2005 055679 A1 | 6/2006 |

OTHER PUBLICATIONS

Provenzano C et al.: "Method for artifact-free circular dichroism measurements based on polarization grating", Optics Letters, OSA, Optical Society of America, Washington, DC, US, vol. 35, No. 11. Jun. 1, 2010 (Jun. 1, 2010), pp. 1822-1824, XP001554372, ISSN: 0146-9592. 001: 10.1364/0L.35.001822 [retrieved on May 24, 2010] the whole document.

(Continued)

*Primary Examiner* — David Porta
*Assistant Examiner* — Faye Boosalis
(74) *Attorney, Agent, or Firm* — Young & Thompson

(57) ABSTRACT

A spectrometer (100) for analyzing the spectrum of an upstream light beam (1), includes an entrance slit (101) and collimating elements (110) suitable for generating, from the upstream light beam, a collimated light beam (10), characterized in that it also includes: a polarization-dependent
(Continued)

diffraction grating (120) suitable for diffracting, at each wavelength (11, 12) of the spectrum of the upstream light beam, the collimated light beam into a first diffracted light beam (11, 12) and a second diffracted light beam (21, 22); optical recombining elements (130) including a planar optical reflecting surface (130) perpendicular to the grating and suitable for deviating at least the second diffracted light beam; and focussing elements (140) suitable for focussing, at each wavelength, the first diffracted light beam and the second diffracted light beam onto one and the same focussing area (141).

15 Claims, 3 Drawing Sheets

(51) Int. Cl.
*G01J 3/02* (2006.01)
*G01J 3/18* (2006.01)
*G02B 27/28* (2006.01)
*G02B 5/18* (2006.01)

(52) U.S. Cl.
CPC ............ *G01J 3/447* (2013.01); *G02B 27/283* (2013.01); *G01N 2201/063* (2013.01); *G01N 2201/0633* (2013.01); *G02B 5/1866* (2013.01)

(56) References Cited

U.S. PATENT DOCUMENTS

| | | |
|---|---|---|
| 2006/0114458 A1 | 6/2006 | Osawa et al. |
| 2010/0225856 A1 | 9/2010 | Escuti et al. |
| 2010/0225876 A1 | 9/2010 | Escuti et al. |

OTHER PUBLICATIONS

Jihwan Kim et al.: "Snapshot imaging spectropolarimeter utilizing polarization gratings", Proceedings of SPIE, Jan. 1, 2008 (Jan. 1, 2008). p. 708603, XP055020635, ISSN: 0277-786X. DOI: 10.1117/12.795719 pp. 708603-708604; figures 1.4.

Elena Nicolescu et al.: "Compact spectrophotometer using polarization-independent liquid crystal tunable optical filter", Proceedings of SPIE, SPIE—International Society for Optical Engineering, US, vol. 6661 Jan. 1, 2007 (Jan. 1, 2007), p. 666105, XP007921936, ISSN: 0277-786X, DOI: 10.1117/12.735152 Retrieved from the Internet: URL:http://www.ece.ncsu.edu/oleg/files-wik i/5/56/SPIE07Nicolescu-LCPG_spectrometer.pdf figures 1, 5.

Nelson V Tabiryan et al.: "The promise of diffractive waveplates", Optics and Photonics News. OSA, Washington. DC. US, vol. 21. No. 3, Jan. 1, 2010 (Jan. 1, 2010). pages 40-45, XP007921937, ISSN: 1047-6938. DOI: 10.1364/0PN.21.3.000040 the whole document.

International Search Report, dated Feb. 3, 2014, from corresponding PCT application.

* cited by examiner

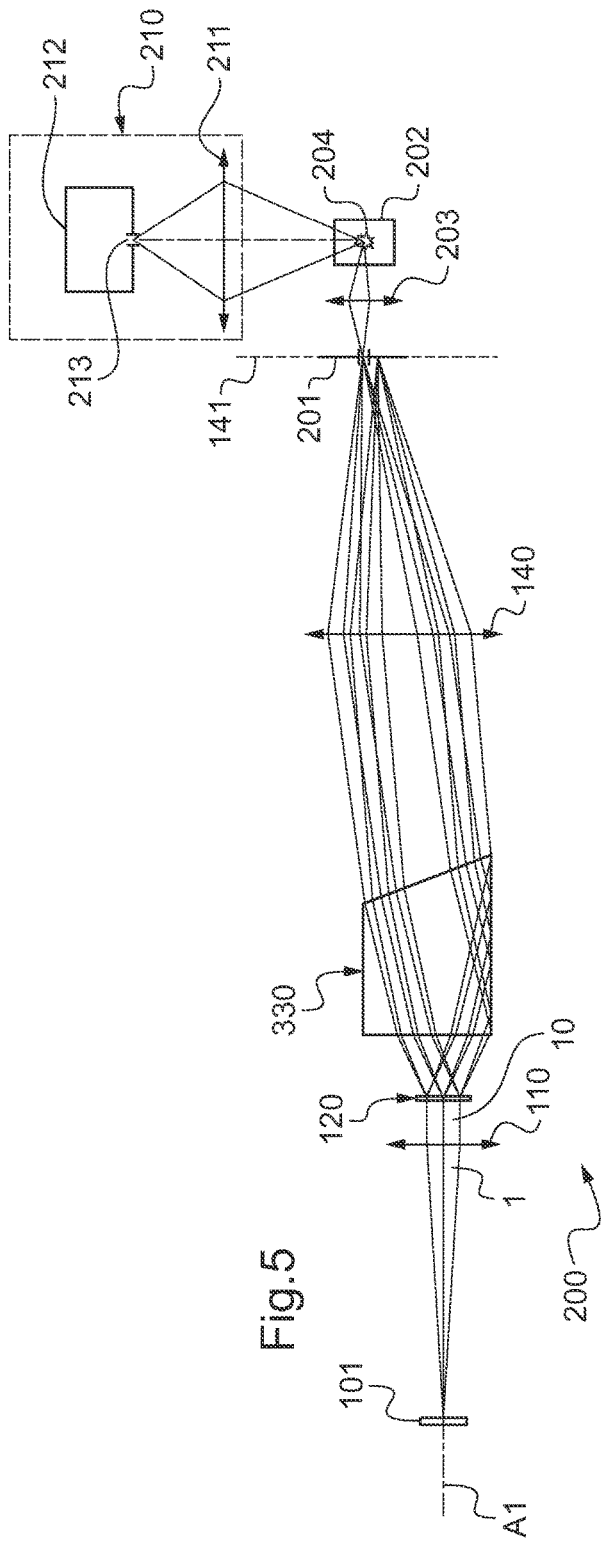
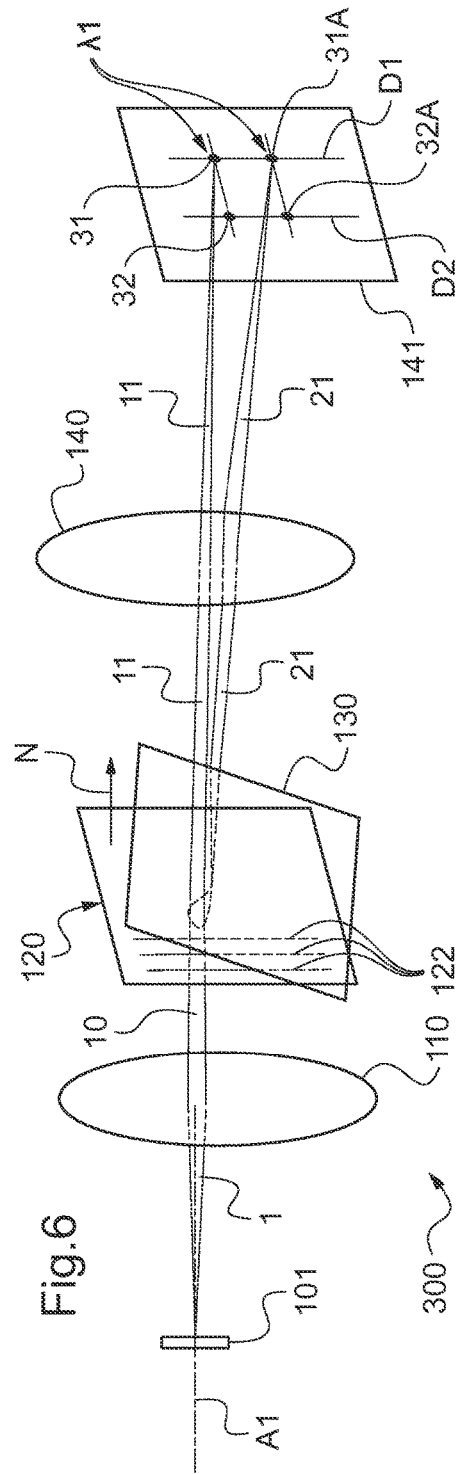

SPECTROMETER FOR ANALYSING THE SPECTRUM OF A LIGHT BEAM

BACKGROUND OF THE INVENTION

Field of the Invention

The invention relates to the field of optical metrology.

More particularly, it relates to a spectrometer of high diffraction efficiency for analysing the spectrum of a light beam or a light source.

The present invention finds a particularly advantageous application when a high efficiency of the spectrometer over a broad spectrum band is desired.

Description of the Related Art

In optical metrology, spectroscopy is a technique that consists in analysing the spectrum of an upstream light beam, whether the latter comes directly from a light source or from an object illuminated by a light source, and in deducing therefrom certain properties of this source or this object.

A spectrometer is an optical instrument allowing to perform such an analysis for a spectrum comprising a plurality of wavelengths.

It is well known that a spectrometer generally includes:
an entrance slit letting the upstream light beam through,
collimation means generating, from the upstream light beam, a collimated light beam,
angular dispersion means intercepting the collimated light beam and angularly dispersing the collimated light beam according to a plurality of wavelengths,
detection means adapted to measure light intensities according to the plurality of wavelengths.

In many applications, as for example Raman spectroscopy or near-infrared spectroscopy, the quantity of light available in the spectrometer, at the detection means, for the spectrum analysis is low. Indeed, a spectrometer carries all the photons of the upstream light beam from the entrance slit to the detection means, with many losses, due in particular to the angular dispersion means.

Moreover, even if the angular dispersion means may be optimised so as to reduce the losses in such a spectrometer, this can be done only on a narrow spectrum band.

Hence, a fast or accurate measurement with such a spectrometer may prove difficult, except using high-performance but expensive detection means.

From documents US2010/0225856A1 and US2010/0225876A1 are known, for example, angular dispersion means comprising so-called achromatic, polarization-separation diffraction gratings, which have a very high diffraction efficiency in the diffraction orders +1 and −1 over a broad spectrum band, in particular in the domain of ultraviolet, visible and infrared wavelengths.

On the other hand, such achromatic polarization-separation diffraction gratings able to be used in a spectrometer are known from the article C. Oh and M. J. Escuti, "Achromatic polarization gratings as highly efficient thin-film polarizing beamsplitters for broadband light", *Proceedings of SPIE*, vol. 6682, no. 668211 (2007).

However, by construction, a polarization-separation diffraction grating operates as a polarization separator. Therefore, the measurement performances of a spectrometer using such a component are not uniform as a function of the polarization state of the upstream light beam, the light intensities measured by the detection means varying with the fluctuations of the polarization state of the upstream light beam.

BRIEF SUMMARY OF THE INVENTION

One of the objects of the invention is to propose a spectrometer whose angular dispersion means have a very high efficiency over a broad spectrum band, allowing to carry with a minimum of losses all the photons of the upstream light beam from the entrance slit to the detection means.

Another object of the invention is to propose a spectrometer having a dispersion efficiency independent of the polarization state of the light beam to be analysed.

Another object of the invention is to propose a spectrometer offering a greater rapidity and a better accuracy of measurement for the analysis of the upstream light beam spectrum.

In order to remedy the above-mentioned drawback of the state of the art, the present invention proposes a spectrometer having improved performances on a broad spectrum band.

For that purpose, the invention relates to a spectrometer for analysing the spectrum of an upstream light beam including:
an entrance slit adapted to let said upstream light beam through,
collimation means adapted to generate, from said upstream light beam, a collimated light beam, and
angular dispersion means arranged so as to intercept said collimated light beam and to angularly disperse said collimated light beam according to a plurality of wavelengths,
wherein:
said angular dispersion means comprise at least one polarization-separation diffraction grating that has a normal to the grating, said polarization-separation diffraction grating being adapted to diffract said collimated light beam into:
at least one first diffracted light beam according to a first diffraction order that is either the diffraction order +1, or the diffraction order −1 of said polarization-separation diffraction grating, said first diffracted light beam being angularly diffracted according to said plurality of wavelengths and having a first polarization state that is circular, and
a second diffracted light beam according to a second diffraction order that is either the diffraction order +1, or the diffraction order −1 of said polarization-separation diffraction grating, said second diffraction order being different from said first diffraction order, said second diffracted light beam being angularly diffracted according to said plurality of wavelengths and having a second polarization state that is circular and orthogonal to said first polarization state, and
including:
optical recombination means arranged at least on an optical path of said second diffracted light beam, downstream of said polarization-separation diffraction grating, said optical recombination means comprising at least one planar optical-reflection surface parallel to said normal to the grating that is adapted to deviate at least said second diffracted light beam, and
focussing means adapted to focus, for each wavelength of said plurality of wavelengths, said first diffracted light beam and said second diffracted light beam to a same focussing surface.

The spectrometer according to the invention hence combines at least one polarization-separation diffraction grating, focussing means and optical recombination means to achieve better performances over a broad spectrum band.

Such a polarization-separation diffraction grating, described for example in the documents US2010/0225856A1 and US2010/0225876A1, has a very high diffraction efficiency in the diffraction orders +1 and −1 over a broad spectrum band, in particular in the domain of ultra-violet, visible and infrared wavelengths.

The spectrometer according to the invention hence allows to exploit the very high diffraction efficiency of the polarization-separation diffraction grating over a broad spectrum band thanks to the optical recombination means that allow, for example at the focussing surface, the recombination of the light beams diffracted by the polarization-separation diffraction grating.

The combined use of a polarization-separation diffraction grating whose sum of diffraction efficiencies in the diffraction order +1 and in the diffraction order −1 is close to 100% for each wavelength of the plurality of wavelengths of the spectrum of the upstream light beam and of optical means for recombining the first diffracted light beam and the second diffracted light beam allows to collect on the focussing surface nearly 100% of the light intensity of the upstream light beam at each wavelength.

Thanks to the focussing means, the light beams, diffracted by the polarization-separation diffraction grating and recombined by the optical recombination means at one wavelength, are focussed on the focussing surface to one focussing point that is spatially separated from the focussing point to which are focussed the light beams diffracted by the polarization-separation diffraction grating and recombined by the optical recombination means at another wavelength.

Hence, the spectrometer according to the invention carries, with almost no loss, the upstream light beam up to the focussing surface.

The spectrometer according to the invention is particularly advantageous insofar as a reduced number of polarization-separation diffraction gratings is necessary to cover a relatively broad wavelength range. This allows in particular to reduce the cost of such a spectrometer.

In the particular case where a single polarization-separation diffraction grating is necessary, this allows not to introduce error in the measurement, wherein the angular dispersion means can be fixed in the spectrometer over the whole measurement range.

Moreover, other advantageous and non-limitative characteristics of the device according to the invention are the following:
- said polarization-separation diffraction grating is planar and has rectilinear and parallel lines;
- said planar optical-reflection surface is parallel to said lines of the polarization-separation diffraction grating, so that said first diffracted light beam and said second diffracted light beam are focussed, for each wavelength of said plurality of wavelengths, by said focussing means to a same focussing point of said focussing surface, said focussing points being separated on said focussing surface according to said plurality of wavelengths;
- said planar optical-reflection surface forms with said lines of the polarization-separation diffraction grating an angle comprised between 0° and 90°, so that said first diffracted light beam and said second diffracted light beam are focussed, for each wavelength of said plurality of wavelengths, by said focussing means to two distinct focussing points of said focussing surface, said two distinct focussing points being separated on said focussing surface;
- said spectrometer includes an exit slit, fixed or mobile, arranged on said focussing surface and adapted to let through said diffracted light beams recombined by said focussing means on said focussing surface;
- said spectrometer includes detection means arranged on said focussing surface and adapted to deliver, for each wavelength of said plurality of wavelengths, a signal relating to the sum of the light intensity diffracted at said wavelength in the diffraction order +1 and of the light intensity diffracted at said wavelength in the diffraction order −1;
- said optical recombination means include a planar mirror arranged so as to reflect, for each wavelength of said plurality of wavelengths, said second diffracted light beam in a direction parallel to said first diffracted light beam;
- said optical recombination means include a prism comprising a base, an entrance face and an exit face inclined with respect to the entrance face, said entrance face and said exit face refracting, for each wavelength of said plurality of wavelengths, said first diffracted light beam and said second diffracted light beam, said second diffracted light beam being deviated, for each wavelength of said plurality of wavelengths, by reflection on said base of the prism between said entrance face and said exit face;
- said optical recombination means include:
  a quarter-wave retardation plate arranged at the exit of the polarization-separation diffraction grating, said quarter-wave retardation plate being adapted to modify said first polarization state and said second polarization state to transform their orthogonal circular polarization states into linear polarization states that are orthogonal to each other,
  a first mirror and a second mirror arranged parallel to each other so as to face each other and perpendicular to said polarization-separation diffraction grating, so that said first mirror, respectively said second mirror, reflects, for each wavelength of said plurality of wavelengths, said first diffracted light beam, respectively said second diffracted light beam, and
  a polarization-recombining cube having a recombination interface and placed between said first mirror and said second mirror, so that said first diffracted light beam reflected by said first mirror is incident on a first entrance face of said polarization-recombining cube and that said second diffracted light beam reflected by said second mirror is incident on a second entrance face of said polarization-recombining cube, one of said reflected diffracted light beams being reflected by said recombination interface and the other reflected diffracted light beam being transmitted by said recombination interface, said first diffracted light beam and said second diffracted light beam being parallel at the exit of said polarization-recombining cube;
- said collimation means comprise an optical collimation system having a collimation numerical aperture and said focussing means comprise an optical focussing system having a focussing numerical aperture that is at least equal to the double of said collimation numerical aperture;
- said detection means include a multi-channel detector;

said detection means include a mobile slit and a single-channel detector;

said spectrometer includes a fluorescence cell and measurement means, said fluorescence cell being arranged downstream of said exit slit so as to be illuminated by said recombined diffracted light beams and to emit a fluorescence signal, said measurement means being adapted to measure the light intensity of said fluorescence signal.

BRIEF DESCRIPTION OF THE DRAWINGS

Several embodiments of the invention are described in detail with reference to the drawings, in which:

FIG. 5 is a schematic view of a spectrometer according to a second embodiment used as a monochromator and comprising a fluorescence cell;

FIG. 6 is a schematic view of a spectrometer according to a third embodiment used as a spectropolarimeter.

DETAILED DESCRIPTION OF THE PREFERRED EMBODIMENTS

Figure 1:
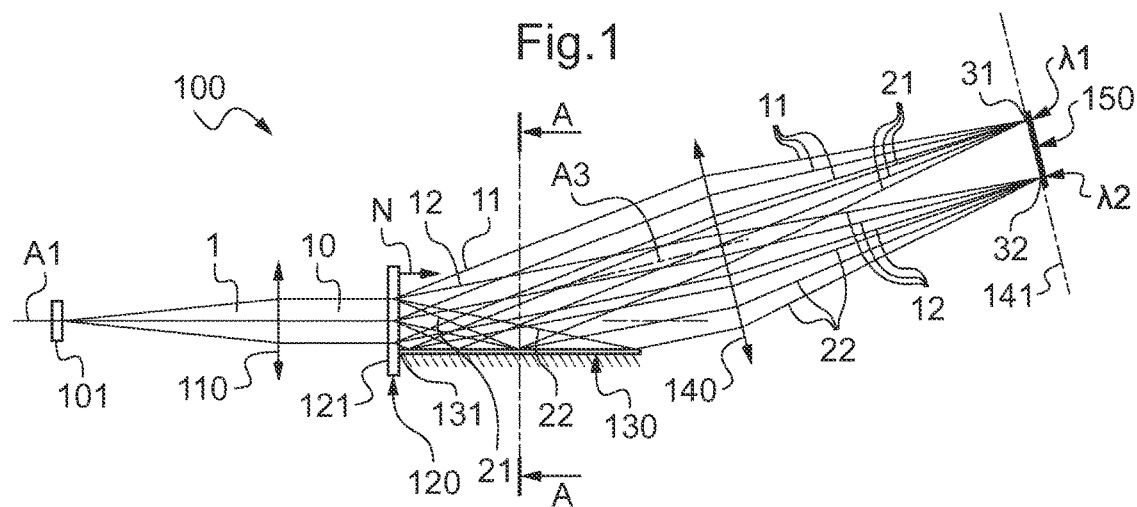
FIG. 1 is a schematic view of a spectrometer according to a first embodiment where the polarization-separation diffraction grating operates in transmission and where the optical recombination means comprise a planar mirror.

In FIG. 1 is shown a first embodiment of a spectrometer 100 according to the invention, intended to analyse the spectrum of an upstream light beam 1.

Figure 2:
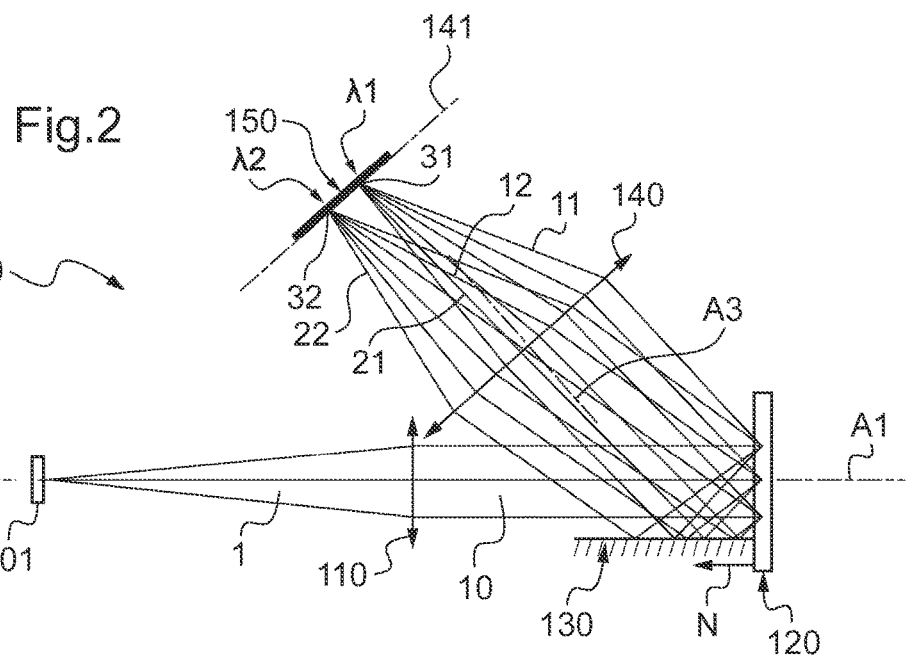
FIG. 2 is a schematic view of a spectrometer according to a first variant of the first embodiment where the polarization-separation diffraction grating operates in reflection and where the optical recombination means comprise a planar mirror.
Figure 3:
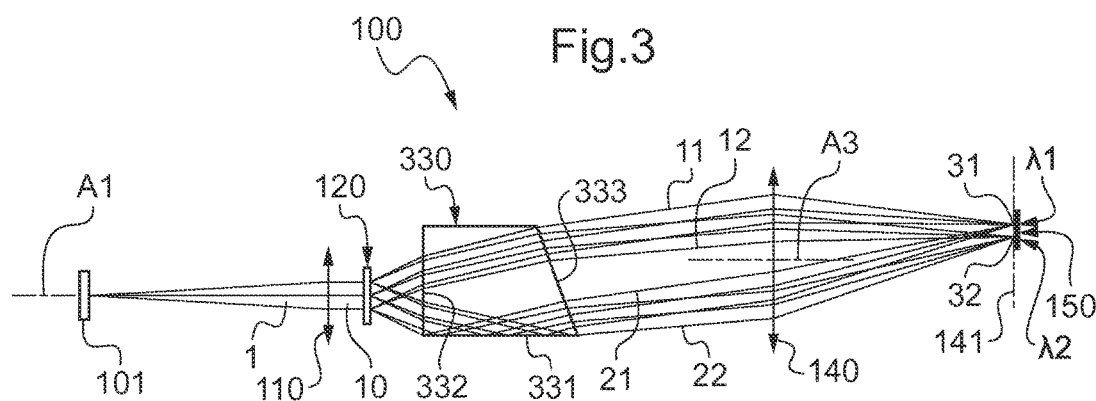
FIG. 3 is a schematic view of a spectrometer according to a second variant of the first embodiment where the polarization-separation diffraction grating operates in transmission and where the optical recombination means comprise a prism.
Figure 4:
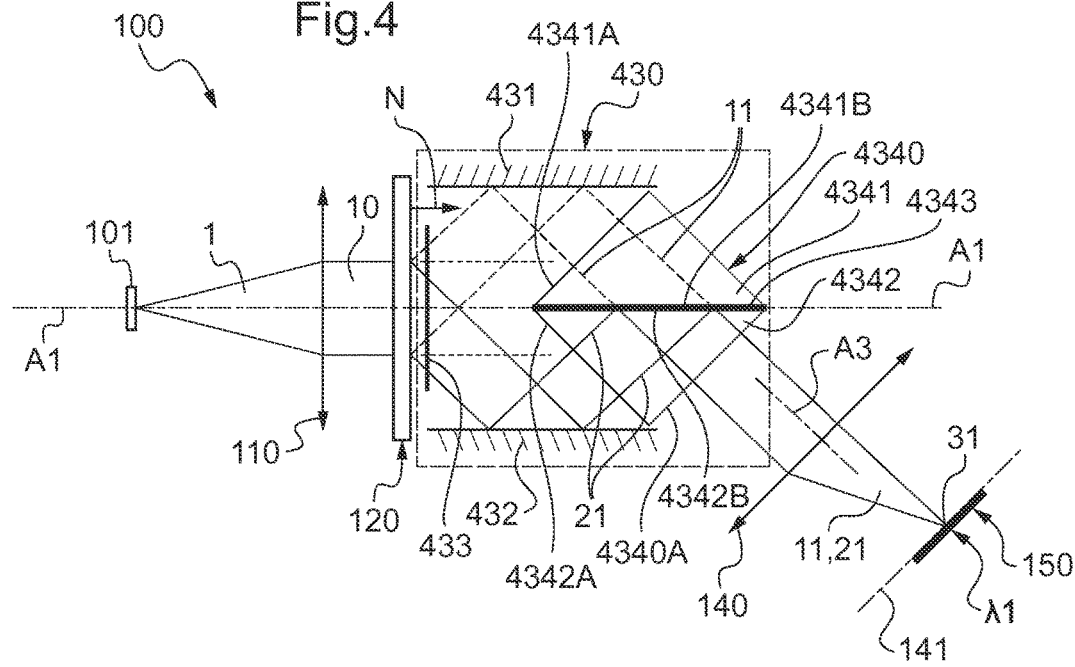
FIG. 4 is a schematic view of a spectrometer according to a third variant of the first embodiment where the polarization-separation diffraction grating operates in transmission and where the optical recombination means comprise a quarter-wave plate, two mirrors and a polarization-recombining cube.

FIGS. 2 to 4 relates to several variants of the first embodiment of a spectrometer 100.

For the sake of simplification and for illustrating the examples of the invention, in the following of the description, two particular wavelengths of the spectrum of the upstream light beam 1 for which the light intensity is non-zero will be considered.

These two particular wavelengths are denoted $\lambda 1$ and $\lambda 2$.

This consideration is not in any way limitative and does not presume of the precise nature of the spectrum of the upstream light beam 1, which may for example be a continuous spectrum, a discrete spectrum, a band spectrum, a line spectrum, or a mixture of all these types of spectrum, or of the spectral extent thereof.

With no limitation either, it will be considered that the upstream light beam 1 is not polarized. Indeed, with no knowledge of the polarization state of the upstream light beam 1, this case is the less restrictive. Moreover, the interest of the invention towards this ignorance a priori of the polarization state of the upstream light beam 1 will be understood from the examples.

Generally, the spectrometer 100 comprises, in the first embodiment and in the variants thereof, an entrance slit 101, collimation means 110, angular dispersion means 120 and detection means 150. The different above-mentioned elements of the spectrometer 100 are included in a casing (not shown) that is opaque to the external light, the entrance slit 101 being located on one of the walls of this casing.

The entrance slit 101 is herein a planar slit of rectangular shape, centred on an optical axis A1 that is perpendicular to the plane of the entrance slit 101.

It will be considered in the different embodiments that the upstream light beam 1 is approximately a divergent light beam formed of a cone of light rays, comprising light rays at the wavelengths $\lambda 1$ and $\lambda 2$, the cone being a cone of revolution about the optical axis A1 and having for apex the centre of the entrance slit 101.

Hence arranged, the entrance slit 101 lets the upstream light beam 1 through.

The spectrometer 100 also includes collimation means 110 that herein comprise an optical collimation system having a collimation numerical aperture.

The optical collimation system 110 has herein an optical axis that is merged with the optical axis A1 and whose object focal point is located at the centre of the entrance slit 101.

Advantageously, the optical collimation system 110 is corrected from the chromatic aberration at least over the spectral extent of the upstream light beam 1.

Hence positioned along the optical axis A1, the collimation means 110 generate, from the upstream light beam 1, a collimated light beam 10.

The collimated light beam 10 is hence formed of light rays at the wavelengths $\lambda 1$ and $\lambda 2$, parallel to each other and to the optical axis A1.

The spectrometer 100 further includes angular dispersion means 120 placed downstream of the collimation means 110 along the optical axis A1.

The angular dispersion means 120 intercept the collimated light beam 10 so that all the light rays at the wavelengths $\lambda 1$ and $\lambda 2$ of the collimated light beam 10 are incident on the angular dispersion means 120 according to the same angle of incidence.

The angular dispersion means 120 angularly disperse the collimated light beam 10 according to the wavelength.

It is understood thereby that the angular dispersion means 120 generate, from the collimated light beam 10 at the wavelengths $\lambda 1$ and $\lambda 2$:

at least one light beam diffracted at the wavelength $\lambda 1$, and at least one light beam diffracted at the wavelength $\lambda 2$, that is angularly separated from the light beam diffracted at the wavelength $\lambda 1$.

In the first embodiment and in the variants thereof, the spectrometer 100 finally includes detection means 150 placed on the optical path of the diffracted light beams.

To analyse the spectrum of the upstream light beam 1, these detection means 150 measure the light intensity of the light beam diffracted at the wavelength $\lambda 1$ and the light intensity of the light beam diffracted at the wavelength $\lambda 2$.

According to the invention, the angular dispersion means 120 comprise at least one polarization-separation diffraction grating.

Generally, a diffraction grating diffracts an incident light ray into one or several diffracted rays propagating in different directions.

With reference to the diffraction grating law, it is hence talked about diffraction orders such as the order 0 and the higher orders: orders ±1, orders ±2, etc. . . . .

It is well known from the physical optics laws that, when they both exist, the rays diffracted in the diffraction orders +1 and −1 propagate in two symmetrical directions with respect to the direction of propagation of the diffracted ray in the diffraction order 0.

It is also known that a planar diffraction grating having rectilinear and parallel lines regularly spaced apart is such that a beam of incident light rays parallel to each other is diffracted into one or several diffracted light beams of parallel light rays.

A polarization-separation diffraction grating is generally a holographic component formed of at least one liquid-crystal diffractive wave plate.

A polarization-separation diffraction grating has the particularity to diffract an incident light beam into at least one ray diffracted in the diffraction order +1 and a ray diffracted in the diffraction order −1, the two diffracted rays being circularly and orthogonally polarized. For example, if the ray diffracted in the diffraction order +1 is circularly polarized to the left, then the ray diffracted in the diffraction order −1 is circularly polarized to the right, and vice versa.

This particularity exists whether the incident light ray is not-polarized or polarized in any way. Indeed, the polarization state of the incident light ray governs only the distribution of the light energy in the diffraction order +1 and in the diffraction order −1.

Preferably, a polarization-separation diffraction grating has moreover, over the wavelength range for which it has been designed, for example over the range 400 nm-800 nm or the range 800 nm-2000 nm, diffraction efficiencies in the diffraction order +1 and in the diffraction order −1 such that their sum is very close to 100%, typically higher than or equal to 90%, and preferentially higher than or equal to 95%.

Indeed, not only a portion of the light incident on a polarization-separation diffraction grating is not diffracted—it is either back-reflected, or absorbed, or scattered—, but also a portion of the light incident on a polarization-separation diffraction grating may be diffracted in the diffraction order 0.

With no limitation, it will be considered hereinafter that the polarization-separation diffraction grating 120 of the spectrometer 100 according to the invention is herein a planar diffraction grating that has a normal N to the grating as shown in FIGS. 1 to 4.

Advantageously, the normal N is herein parallel to the optical axis A1 so that the polarization-separation diffraction grating 120 is in the four embodiments shown in FIGS. 1 to 4 placed perpendicular to the optical axis A1 in such a manner that the collimated light beam 10 is in normal incidence on an entrance face 121 of the polarization-separation diffraction grating 120.

By analogy with a conventional diffraction grating, such as that described hereinabove, it will also be considered herein that the polarization-separation diffraction grating 120 has rectilinear and parallel lines 122, regularly spaced apart (see FIG. 1A). These lines 122 are not protrusions but correspond to lines of equal orientation of the liquid crystals constituting the diffractive wave plate of the polarization-separation diffraction grating 120.

So designed, a light ray of the collimated light beam 10 incident on the polarization-separation diffraction grating 120 is diffracted into diffracted beams that are all coplanar and contained in a diffraction plane of the polarization-separation diffraction grating 120.

This diffraction plane is the plane that contains the incident light ray and that is perpendicular to the lines 122 of the polarization-separation diffraction grating 120. The diffraction plane is hence such that the normal N to the grating is parallel to this diffraction plane.

The optical behaviour of a polarization-separation diffraction grating as just described hereinabove remains valid for any wavelength for which the polarization-separation diffraction grating has been designed.

Are dependent on the wavelength: the directions of propagation of the diffracted rays and the diffraction efficiencies of the different diffraction orders.

Are not dependent on the wavelength: the "left" or "right" character of the polarization of the rays diffracted in the diffraction orders +1 and −1, i.e. two rays at different wavelengths diffracted in the diffraction order +1 are polarized circularly in the same direction (for example the left), the two rays diffracted in the diffraction order −1 at these two wavelengths being also polarized circularly in the same direction (herein the right) and with an orthogonal polarization.

It will hence be understood that the polarization-separation diffraction grating 120 of the spectrometer 100 according to the invention diffracts the collimated light beam 10 into:

at least one first diffracted light beam 11, 12 according to a first diffraction order that is either the diffraction order +1 or the diffraction order −1 of the polarization-separation diffraction grating 120, the first diffracted light beam 11, 12 being angularly diffracted as a function of the plurality of wavelengths and having a first polarization state that is circular, and a second diffracted light beam 21, 22 according to a second diffraction order that is either the diffraction order +1 or the diffraction order −1 of said polarization-separation diffraction grating 120, said second diffraction order being different from said first diffraction order, the second diffracted light beam 21, 22 being angularly diffracted as a function of the plurality of wavelengths and having a second polarization state that is circular and orthogonal to the first polarization state.

With no limitation, it will be considered in the four embodiments of the invention that the first diffracted light beam 11, 12 is diffracted in the diffraction order +1 and that the second diffracted light beam 21, 22 is diffracted in the diffraction order −1.

Hence, at the wavelength λ1, Ie collimated light beam 10 is diffracted into a first diffracted light beam 11 at the wavelength λ1 in the diffraction order +1 and a second diffracted light beam 21 at the wavelength λ1 in the diffraction order −1.

Likewise, at the wavelength λ2, the collimated light beam 10 is diffracted into a first diffracted light beam 12 at the wavelength λ2 in the diffraction order +1 and a second diffracted light beam 22 at the wavelength λ2 in the diffraction order −1.

With no limitation either (see supra), it will also be considered that the first diffracted light beam 11 at the wavelength λ1 and the first diffracted light beam 12 at the wavelength λ2 have a first left circular polarization state, and that the second diffracted light beam 21 at the wavelength λ1 and the second diffracted light beam 22 at the wavelength λ2 have a second right circular polarization state, which is hence orthogonal to the first polarization state.

In the optical configurations shown in FIGS. 1 to 4, the diffraction order 0 is parallel to the optical axis A1. Hence, as the collimated light beam 10 is in normal incidence on the entrance face 121 of the polarization-separation diffraction grating 120 (see supra), at the exit of the polarization-separation diffraction grating 120, the first diffracted light beam 11 at the wavelength λ1 in the diffraction order +1 and the second diffracted light beam 21 at the wavelength λ1 in the diffraction order −1 are symmetrical with respect to the optical axis A1.

Likewise, at the exit of the polarization-separation diffraction grating 120, the first diffracted light beam 12 at the wavelength λ2 in the diffraction order +1 and the second diffracted light beam 22 at the wavelength λ2 in the diffraction order −1 are symmetrical with respect to the optical axis A1.

Still according to the invention, the spectrometer 100 also includes focussing means 140.

In the four variants, the focussing means 140 comprise an optical focussing system having a focussing numerical aperture and an optical focussing axis A3.

Preferably, the optical focussing system 140 is herein arranged and oriented in the spectrometer 100 so that its optical focussing axis A3 is coplanar and secant with the optical axis A1.

The focussing means 140 focus the first diffracted light beam 11, 12 and the second diffracted light beam 21, 22 on a focussing surface that is for example formed of a focussing plane 141.

In the different variants of the first embodiment of the spectrometer 100 shown in FIGS. 1 to 4, the detection means 150 are arranged on the focussing surface 141.

More precisely here, the detection means 150 are planar detection means whose detection plane is the focussing plane 141 of the optical focussing system 140.

The way the detection means 150 operate in the spectrometer 100 will be detailed hereinafter.

The spectrometer 100 moreover includes optical recombination means 130; 330; 430.

The optical recombination means 130; 330; 430 are arranged at least on an optical path of the second diffracted light beam 21, 22, downstream of the polarization-separation diffraction grating 120.

In the first embodiment and in the variants thereof shown in FIGS. 1 to 4, the optical recombination means 130; 330; 430 are arranged between the polarization-separation diffraction grating 120 and the focussing means 140.

The optical recombination means 130; 330; 430 comprise a planar optical-reflection surface 130; 331; 432 that is parallel to the normal N to the grating.

Figure 1A:
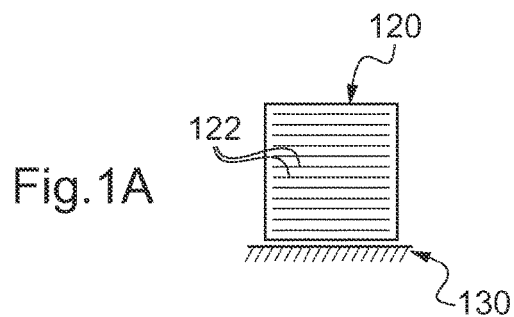
FIG. 1A is a schematic view according to the plane A-A of FIG. 1, showing the planar mirror and the lines of the polarization-separation diffraction grating of FIG. 1.

Moreover, in the first embodiment and in the variants thereof shown in FIGS. 1 to 4, the planar optical-reflection surface 130; 331; 432 is also parallel to the lines 122 of the polarization-separation diffraction grating 120, as shown in FIG. 1A.

Hence oriented, the optical recombination means 130; 330; 430 then deviate at least the second diffracted light beam 21, 22 so that the first diffracted light beam 11, 12 and the second diffracted light beam 21, 22 are focussed by the focusing means 140 on the focusing surface 141.

More precisely, the first diffracted light beam 11,12 and the second diffracted light beam 21, 22 are focussed by the focusing means 140 to a same focusing point (31, 32) of the focusing surface 141, and hence of the detection means 150 for a wavelength.

Still more precisely, the optical focussing system 140 focusses:
the first diffracted light beam 11 at the wavelength λ1 and the second diffracted light beam 21 at the wavelength λ1 to a same first focussing point 31 on the focussing surface 141, and hence on the detection means 150, and
the first diffracted light beam 12 at the wavelength λ2 and the second diffracted light beam 22 at the wavelength λ2 to a same second focussing point 32 on the focussing surface 141, and hence on the detection means 150, this second focussing point 32 being spatially separated from the first focussing point 31.

This spatial separation as a function of the wavelength of the focussing points on the focussing surface 141, and hence on the detection means 150, allows to measure separately the light intensity at the wavelength λ1 and the light intensity at the wavelength λ2.

The detection means 150 hence deliver, for each of the two wavelengths λ1 and λ2, a signal relating to the sum of the light intensity diffracted in the diffraction order +1 and of the light intensity diffracted at said wavelength in the diffraction order −1.

As indicated above, the sum of the diffraction efficiencies in the diffraction order +1 and in the diffraction order −1 of a polarization-separation diffraction grating 120 is very high.

Thanks to the combined use of the polarization-separation diffraction grating 120, optical recombination means 130; 330; 430 and focussing means 140, it is possible to exploit this particular property of the polarization-separation diffraction gratings so that the spectrometer 100 according to the invention has a high transmission between the entrance slit 101 and the detection means 150 so as to improve the rapidity and the accuracy of analysis of the spectrum of the upstream light beam 1.

The different variants of the invention described hereinabove, and in particular the optical recombination means 130; 330; 430, will be described in more detail hereinafter.

Moreover, in order to simplify the description, the different variants will be described hereinafter only according to a wavelength λ1, it being understood that the operation of the spectrometer 100, and in particular of its optical recombination means 130; 330; 430, is identical for each wavelength belonging to the spectrum of the upstream light beam 1 for which the spectrometer 100 has been designed.

In FIG. 1 is shown a spectrometer 100 according to a first embodiment, in which the polarization-separation diffraction grating 120 operates in transmission and in which the optical recombination means 130 include a planar mirror, the planar optical-reflection surface of the optical recombination means 130 being formed by the reflective surface of the planar mirror.

This mirror 130 is arranged downstream of the polarization-separation diffraction grating 120, between the latter and the optical focussing system 140.

The mirror 130 is placed in the low portion of the polarization-separation diffraction grating 120, towards which the second diffracted light beam 21 at the wavelength λ1 propagates.

The mirror 130 is oriented so that it is, on the one hand, parallel to the normal N to the polarization-separation diffraction grating 120 and, on the other hand, parallel to the lines 122 of the polarization-separation diffraction grating 120 (see in particular FIG. 1A).

Advantageously, the mirror 130 comprises a lateral ridge 131 that is placed side by side with the exit face 122 of the polarization-separation diffraction grating 120.

Hence positioned and oriented in the spectrometer 100, the mirror 130 reflects the second diffracted light beam 21 at the wavelength λ1.

The size of the mirror 130 according to the optical axis A1 is chosen great enough so that the mirror 130 reflects, at each wavelength, the second diffracted light beam 21, 22.

By reflection, the mirror 130 deviates the second diffracted light beam 21 at the wavelength λ1 so that the second diffracted light beam 21 is parallel to the first diffracted light beam 11 at the wavelength λ1.

The first diffracted light beam 11 and the second diffracted light beam 21 being parallel, they are focussed by the optical focussing system 140 to the first focussing point 31 of the detection means 150.

In this optical configuration, the optical focussing system 140 must hence have a focussing numerical aperture that is the double of the collimation numerical aperture of the optical collimation system 110.

The behaviour of the above-described spectrometer 100 is also valid for the wavelength λ2 and the first diffracted light beam 12 at the wavelength λ2 and the second diffracted light beam 22 at the wavelength λ2 are focussed by the optical focussing system 140 to the second focussing point 32 of the detection means 150.

The first diffracted light beam 12 at the wavelength λ2 being not diffracted in the same direction as the first diffracted light beam 11 at the wavelength λ1, the second focussing point 32 is spatially separated from the first focussing point 31. Moreover, this is true for each wavelength of the spectrum of the upstream light beam 1.

In addition, the polarization-separation diffraction grating 120, the mirror 130 and the optical focussing system 140 are herein arranged in the spectrometer 100 such that the different focussing points on the detection means 150 are aligned with each other.

The detection means 150 include a multi-channel detector herein formed of a linear array of CCD sensors placed such that the focussing points are aligned on the line of CCD sensors.

The first focussing point 31 and the second focussing point 32 are centred on different pixels of the linear array of CCD sensors so that the multi-channel detector 150 delivers:
- a signal relating to the sum of the light intensity diffracted at the wavelength λ1 in the diffraction order +1 and the light intensity diffracted at the wavelength λ1 in the diffraction order −1, this sum being close to 100% of the light intensity of the upstream light beam 1 at the wavelength λ1, and
- a signal relating to the sum of the light intensity diffracted at the wavelength λ2 in the diffraction order +1 and of the light intensity diffracted at the wavelength λ2 in the diffraction order −1, this sum being also close to 100% of the light intensity of the upstream light beam 1 at the wavelength λ2.

This is true for all the wavelengths belonging to the spectrum of the upstream light beam 1, the detection means 150 then measure, according to the wavelength, the light intensities of the upstream light beam 1 to deduce its spectrum therefrom.

It is besides known that the spectral resolution (expressed in nanometers) of the multi-channel detector is in particular function of the size of the CCD sensors and of the spacing thereof.

Generally, the spectral resolution of a spectrum is function of the power of dispersion of the angular dispersion means, of the possible optical aberrations of the collimation means and of the focussing means, as well as the spatial resolution of the detection means.

As a variant, the multi-channel detector could for example be formed of a matrix of CCD sensors.

As another variant, the detection means could have a mobile slit and a single-channel detector. The mobile slit has a shape and size that are those of the image of the entrance slit by the optical collimation system, the polarization-separation diffraction grating and the optical focussing system. The single-channel detector is a single detector, for example a silicon, germanium, InGaAs, InAs, InSb, PbS, PbSe or HgCdTe photodiode, an avalanche photodiode, a photo-multiplier tube.

The second variant of the spectrometer 100, shown in FIG. 2, has an architecture similar to the first variant of the spectrometer 100 of FIG. 1, except that the polarization-separation diffraction grating 120 of the spectrometer 100 operates in reflection rather than in transmission.

Similarly to the first variant, the mirror 130 reflects the second light beam 21, 22 diffracted by the polarization-separation diffraction grating 120 at the different wavelengths λ1, λ2 of the spectrum.

In these conditions, it is then provided that the distance between the optical collimation system 110 and the polarization-separation diffraction grating 120 is sufficient so that the mirror 130 can be arranged between the polarization-separation diffraction grating 120 and the optical collimation system 110.

Moreover, it is also provided that the distance between the optical collimation system 110 and the polarization-separation diffraction grating 120 is great enough so that the diffracted light beams 11, 12, 21, 22 are not intercepted by the optical collimation system 110.

In FIG. 3 is shown a second variant of the first embodiment of the spectrometer 100 in which the polarization-separation diffraction grating 120 operates in transmission and in which the optical recombination means 330 include a prism.

Advantageously, this prism 330 is a mineral-glass optical prism whose faces are polished. It includes a base 331, an entrance face 332 and an exit face 333.

The entrance face 332 is herein a planar face that is parallel to the polarization-separation diffraction grating 120 (the entrance face 332 being hence perpendicular to the optical axis A1) and that is centred on the optical axis A1.

The exit face 333 of the prism 330 is also a planar face. It is inclined with respect to the entrance face 332.

The travel of the first diffracted light beam 11 at the wavelength λ1 then the travel of the second diffracted light beam 21 at the wavelength λ1 will be described hereinafter.

As shown in FIG. 3, the first diffracted light beam 11 is incident on the entrance face 332 of the prism 330 and is refracted by the latter.

The first diffracted light beam 11 then propagates in parallel in the prism 330, then is incident on the exit face 333 of the prism 330 that in turn refracts it.

The first diffracted light beam 11 then propagates, still in parallel, towards the optical focussing system 140, simply deviated by the prism 330 with respect to its initial direction at the exit of the polarization-separation diffraction grating 120.

Still according to FIG. 3, the second diffracted light beam 21 is incident on the entrance face 332 of the prism 330 and is refracted by the latter.

The first diffracted light beam 11 then propagates in parallel in the prism 330.

As the first diffracted light beam 11 and the second diffracted light beam 21 are symmetrical with respect to the optical axis A1 at the exit of the polarization-separation diffraction grating 120, before being incident on the entrance face 332 of the prism 330 to be refracted thereon, and as the entrance face 332 of the prism 330 is perpendicular to the optical axis A1, the first diffracted light beam 11 and the second diffracted light beam 21 are also symmetrical after refraction on the entrance face 332.

The base 331 of the prism 330 being oriented in the plane of incidence in the same way as the mirror 130 of FIG. 1 and being that way perpendicular to the entrance face 332, the parallel light rays to the second diffracted light beam 21 are all incident on the base 331 of the prism 330 with an angle of incidence higher than the angle of total reflection of this prism 330.

Hence, the second diffracted light beam 21 is totally reflected on the base 331 of the prism 330 by total internal reflection, between the entrance face 332 and the exit face 333. The base 331 of the prism 330 thus constitutes, for the variant of FIG. 3, the planar optical-reflection surface of the optical recombination means 330.

The second diffracted light beam 21 is hence thereafter incident with the same angle of incidence as the first diffracted light beam 11 on the exit face 333 of the prism 330 that in turn refracts it.

The second diffracted light beam 21 then propagates towards the optical focussing system 140, in parallel to the first diffracted light beam 11.

Advantageously, the entrance face 332 and the exit face 333 are coated with an anti-reflective treatment allowing, on the one hand, to reduce the losses by reflection on the entrance face 332 and on the exit face 333, and on the other hand, to limit the formation of spurious light beams that could reduce the accuracy of the light intensity measurements performed by the detection means 150.

In FIG. 4 is shown a third variant of the first embodiment of the spectrometer 100 in which the polarization-separation diffraction grating 120 also operates in transmission and in which the optical recombination means 430 include a retardation plate 433, a first mirror 431, a second mirror 432, and a polarization-recombination cube 4340.

For the sake of clarity, only the light rays of the wavelength λ1 have been shown in FIG. 4.

The retardation plate 433 is arranged at the exit of the polarization-separation diffraction grating 120, in parallel to the latter. The retardation plate 433 is preferably located at a very close distance from the polarization-separation diffraction grating 120, for example 1 millimeter, so that the retardation plate 433 intercepts the first diffracted light beam 11 and the second diffracted light beam 21.

As a variant, the retardation plate may be placed side by side with the exit face of the polarization-separation diffraction grating so that they form only a single and same optical component.

The retardation plate 433 is an achromatic quarter-wave plate optimized to operate at least in the wavelength range of the polarization-separation diffraction grating 120.

Advantageously, the retardation plate 433 has a great angular acceptance.

This retardation plate 433 modifies the respective polarization states of the first diffracted light beam 11 and of the second diffracted light beam 21 that are circular and orthogonal polarization states at the entrance of the retardation plate 433, so that:

the first polarization state is transformed into a linear polarization state, and the second polarization state is transformed into a linear polarization state orthogonal to the first polarization state, the retardation plate 433 keeping the property of orthogonality.

The retardation plate 433 is oriented so that the first polarization state at the exit of this retardation plate 433 corresponds to the polarization state transmitted by the polarization-recombining cube 4340 (see hereinafter) and so that the second polarization state at the exit of the retardation plate 433 corresponds to the polarization state reflected by this polarization-recombining cube 4340 (see hereinafter).

The retardation plate 433 herein does not deviate the first diffracted light beam 11, nor the second diffracted light beam 21.

The second mirror 432 of the optical recombination means 430 is a planar mirror herein arranged perpendicular to the plane of incidence, in the same way with respect to the polarization-separation diffraction grating 120 and to the optical axis A1 as the planar mirror 130 of the first embodiment.

This second mirror 432 constitutes, in this third variant, the planar optical-reflection surface of the optical recombination means 430.

The first mirror 431 is a planar mirror arranged parallel to the second mirror 432 in order to face it. The first mirror 431 is hence also perpendicular to the polarization-separation diffraction grating 120.

So arranged, it is understood that:

the first mirror 431 reflects, at the wavelength λ1, the first light beam 11 diffracted at the wavelength λ1, and that the second mirror 432 reflects, at the same wavelength λ1, the second light beam 21 diffracted at the wavelength λ1.

After reflection on the first mirror 431 and on the second mirror 432, the first diffracted light beam 11 and the second diffracted light beam 21 remain symmetrical with respect to the optical axis A1.

Moreover, the reflections on the first mirror 431 and on the second mirror 432 do not modify the first polarization state nor the second polarization state that remain linear polarization states that are orthogonal to each other.

The polarization-recombining cube 4340 is placed between the first mirror 431 and the second mirror 432 so that:

the first diffracted light beam 11 reflected by the first mirror 431 is incident according to a first angle of incidence on a first entrance face 4341A of the polarization-recombining cube 4340, the first diffracted light beam 11 being transmitted by this first entrance face 4341A in the first prism 4341, and that:

the second diffracted light beam 21 reflected by the second mirror 432 is incident according to a second angle of incidence equal to the first angle of incidence on a second entrance face 4342A of the polarization-recombining cube 4340, the second diffracted light beam 21 being transmitted by this second entrance face 4342A in a second prism 4342.

Advantageously, and for the same reasons as above, the first entrance face 4341A and the second entrance face 4342A of the polarization-recombining cube 4340 are coated with an anti-reflective treatment.

The polarization-recombining cube 4340 is hence formed of the first prism 4341 and of the second, identical, prism 4342, which are both rectangular isosceles straight prisms.

The first prism 4341 comprises the entrance face 4341A of the polarization-recombining cube 4340 and a hypotenuse face 4341B.

Likewise, the second prism 4342 comprises the entrance face 4342A of the polarization-recombining cube 4340, a hypotenuse face 4342B, and a last face 4340A forming an exit face of the polarization-recombining cube 4340.

The first prism 4341 and the second prism 4342 are placed side by side through their hypotenuse faces 4341B, 4342B by means of an optical glue to form a recombination interface 4343 of the polarization-recombining cube 4340.

The first prism 4341 and the second prism 4342, which are herein identical, are made of mineral glass, for example glass of the BK7 type, and their hypotenuse faces 4341B, 4341B are coated with a filter that has for function, for the wavelengths λ1 and λ2, to:

transmit the light rays that are incident on the hypotenuse faces 4341B, 4342B and that are linearly polarized, and to:

reflect the light rays that are incident on the hypotenuse faces 4341B, 4342B, and that are polarized linearly and orthogonally to the light rays transmitted by these hypotenuse faces 4341B, 4342B.

In particular, the polarization-recombining cube 4340 is such that:

the first diffracted light beam 11, that propagates in the first prism 4341 according to a first linear polarization state and that is incident on the hypotenuse face 4341B, at the recombination interface 4343, is transmitted by the recombination interface 4343;

the second diffracted light beam 21, that propagates in the second prism 4342 according to a second linear polarization state, orthogonal to the first polarization state, and that is incident to the hypotenuse face 4341B, at the level of the recombination interface 4343, is reflected by the recombination interface 4343.

Hence, as the first diffracted light beam 11 and the second diffracted light beam 21 are incident with the same angle of incidence on the entrance faces 4341A, 4342A of the polarization-recombining cube 4340, after transmission of the first diffracted light beam 11 and reflection of the second diffracted light beam 21 through the recombination interface 4343, the first diffracted light beam 11 and the second diffracted light beam 21 are herein superimposed to each other and propagate in parallel in the second prism 4342 to be incident, in normal incidence, on the exit face 4340A of the polarization-recombining cube 4340.

Transmitted by this exit face 4340A, the first diffracted light beam 11 and the second diffracted light beam 21 are parallel, and even herein superimposed to each other, at the exit of the polarization-recombining cube 4340 and propagate in parallel towards the focussing means 140.

As the first diffracted light beams and the second diffracted light beams are symmetrical before transmission or reflection by the recombination interface 4343 of the polarization-recombining cube 4340 for each wavelength, these light beams are superimposed to each other and propagate in parallel at the exit of the polarization-recombining cube 4340 at each wavelength.

Advantageously, and for the same reasons as above, the exit face 4340A of the polarization-recombining cube 4340 is also coated with an anti-reflective treatment.

Thanks to the superimposition of the first diffracted light beam 11 and of the second diffracted light beam 21 at the exit of the polarization-recombining cube 4340, the focussing numerical aperture of the optical focussing system may be lower than the double of the collimation numerical aperture.

It has been shown in FIG. 5 a second embodiment of a spectrometer 200.

This spectrometer 200 is similar to the third variant of the first embodiment shown in FIG. 3, in that it includes the following identical elements: the entrance slit 101, the collimation means 110, the angular dispersion means 120, the optical recombination means 330 and the focussing means 140.

As a variant, the spectrometer according to this second embodiment could, for example, include an entrance slit, collimation means, angular dispersion means, optical recombination means and focussing means identical to the first embodiment or to the variants thereof shown in FIGS. 1, 2 and 4.

The spectrometer 200 includes an exit slit 201 arranged on the focussing surface 141 of the focussing means 140, i.e. in the focussing plane of the focussing lens.

The exit slit 201 is herein mobile and may be translated in the focussing plane 141 to select a particular wavelength of the spectrum of the upstream light beam 1.

More precisely, in the configuration shown in FIG. 5, the exit slit 201 is arranged in the focussing plane so as to let through the diffracted light beams 11, 21 that are recombined by the focussing means 140 in the focussing plane.

As a variant, the exit slit could for example be fixed, so that, by construction, the spectrometer let through only a single and same wavelength determined by the fixed position of the exit slit.

The spectrometer 200 further includes a fluorescence cell 202 placed downstream of the exit slit 201, on the optical path of the diffracted light beams 11, 21.

The spectrometer 200 also includes an imaging lens 203 that forms the image of the exit slit 201 on a study volume 204 of the fluorescence cell 202 so that this fluorescence cell 202 is illuminated by the diffracted light beams 11, 21 passing through the exit slit 201.

The fluorescence cell 202 herein comprises a small vat made of transparent glass containing a solution of a product of which it is desired to measure the fluorescence signal at a predefined excitation wavelength or the fluorescence spectrum.

When the fluorescence cell 202, in particular the study volume 204, is illuminated by the diffracted light beams 11, 21 at the wavelength λ1, this study volume 204 then emits a fluorescence signal in all the directions, over a wavelength band going from 300 nm to 1100 nm.

This fluorescence signal is then collected by measurement means 210 that measure the light intensity of the fluorescence signal emitted by the fluorescence cell 202.

For that purpose, the measurement means 210 include an optical collection system 211 of the fluorescence signal allowing to collect a portion of the fluorescence signal emitted by the fluorescence cell 202.

This optical collection system 211 has herein an optical collection axis A2 perpendicular to the optical axis A1 of the spectrometer 200.

This configuration allows to collect the fluorescence signal without being bothered by the diffracted light beams 11, 21 incident on the fluorescence cell 202.

The measurement means 210 also include a second spectrometer 212 provided with an entrance measurement slit 213.

The optical collection system 211 forms the image of the study volume 204 of the fluorescence cell 202 in the plane of the entrance measurement slit 213.

The second spectrometer 212 then measures the light intensity of the fluorescence signal emitted by the fluorescence cell 202 as a function of the wavelength.

The measurement means 210 hence allow to analyse the response of the fluorescence cell 202 for the wavelength λ1.

In FIG. 6 is shown a third embodiment of a spectrometer 300 also allowing to determine the polarization state of the upstream light beam 1.

This spectrometer 300 of FIG. 6 is similar to the first embodiment shown in FIG. 1, in that it includes the following identical elements: an entrance slit 101, an optical collimation system 110, a polarization-separation diffraction grating 120, a planar mirror 130 and a focussing lens 140.

As a variant, the spectrometer according to this third embodiment could, for example, include an entrance slit, collimation means, angular dispersion means, optical recombination means and focussing means identical to the variants of the first embodiment shown in FIGS. 2 to 4.

In this third embodiment, and as well shown in FIG. 6, the mirror 130 is arranged and oriented with respect to the polarization-separation diffraction grating 120 so that the planar optical-reflection surface, consisted by the reflective surface of the mirror 130, is not parallel to the lines 122 of the polarization-separation diffraction grating 120 but forms with them an angle comprised between 0° and 90°.

So arranged, the optical recombination means 130 are such that the first diffracted light beam 11 and the second diffracted light beam 21 are focussed, for the wavelength λ1, by the focussing lens 140 in two distinct focussing points 31, 31A of the focussing surface 141.

In the focussing plane, the two distinct focussing points 31, 31A are then separated on said focussing surface 141, and are aligned according to a straight line D1.

Similarly, the first diffracted light beam 12 and the second diffracted light beam 22 (beams not shown) are focussed, for the wavelength λ2, by the focussing lens 140 to two distinct focussing points 32, 32A of the focussing surface 141, which are aligned along a straight line D2 of the focussing plane, parallel to the straight line D1 for the wavelength λ1.

Moreover, the focussing points 31, 31A at the wavelength 21 are spaced along the straight line D1 by the same distance as the focussing points 32, 32A at the wavelength λ2 along the straight line D2.

It will be considered in the following that the first diffracted light beam 11 has a first intensity I11 at the wavelength λ1 and the second diffracted light beam 21 has a second intensity I21 at the wavelength λ1.

According to what has been described hereinabove, the polarization-separation diffraction grating 120 is such that the ratio between the respective intensities I11 and I21 of the first and second diffracted light beams 11, 21 at the wavelength λ1 is function of the polarization state of the upstream light beam 1 in the plane of the entrance slit 101.

It is moreover also the same for the first and second diffracted light beams 12, 22 at the wavelength λ2.

Hence, by placing detection means (not shown) in the plane of the focussing surface 141 so as to measure separately the relative intensities of the first and second diffracted light beams 11, 21, 12, 22 for each of the wavelengths contained in the spectrum of the upstream light beam 1, it is not only possible to determine the spectrum of the upstream light beam 1 for the two natural polarization states of the polarization-separation diffraction grating 120, but especially the polarization state of the upstream light beam 1 according to the wavelength. A spectropolarimeter is hence obtained.

Generally, the spectrometer of the invention allows to recombine the diffracted beams by a polarization-separation diffraction grating in the orders +1 and −1. In a way, the spectrometer of the invention superimposes the diffraction orders +1 and −1, hence allowing to exploit at best the diffraction efficiency of such a grating.

Generally, the spectrometer according to the invention has a high efficiency, close to 100% over a broad spectrum band, and that independently of the polarization state of the upstream light beam, wherein the latter can be polarized or not.

A realization of a spectrometer according to the invention has shown, with respect to a standard spectrometer implementing a conventional diffraction grating, an improvement of the efficiency of the spectrometer by a multiplicative factor comprised between two and three, for different lines of a Hg—Ar lamp on the wavelength band comprised between 500 nm and 760 nm.

The invention claimed is:

1. A spectrometer for analyzing the spectrum of an upstream light beam, the spectrometer comprising:
   an entrance slit that lets said upstream light beam therethrough;
   a collimation system configured to generate, from said upstream light beam, a collimated light beam;
   an angular dispersion device configured to intercept said collimated light beam and to angularly disperse said collimated light beam according to a plurality of wavelengths, said angular dispersion device comprising at least one polarization-separation diffraction grating that has a normal N to the grating, said polarization-separation diffraction grating being configured to diffract said collimated light beam into:
      at least one first diffracted light beam according to a first diffraction order that is either the diffraction order +1, or the diffraction order −1 of said polarization-separation diffraction grating, said first diffracted light beam being angularly diffracted according to said plurality of wavelengths and having a first polarization state that is circular, and
      a second diffracted light beam according to a second diffraction order that is either the diffraction order +1, or the diffraction order −1 of said polarization-separation diffraction grating, said second diffraction order being different from said first diffraction order, said second diffracted light beam being angularly diffracted according to said plurality of wavelengths and having a second polarization state that is circular and orthogonal to said first polarization state;
   an optical recombination system disposed at least on an optical path of said second diffracted light beam, downstream of said polarization-separation diffraction grating, said optical recombination system comprising at least one planar optical-reflection surface parallel to said normal N to the grating that is configured to deviate at least said second diffracted light beam; and
   a focusing system configured to focus, for each wavelength of said plurality of wavelength, said first diffracted light beam and said second diffracted light beam to a same focusing surface.

2. The spectrometer according to claim 1, wherein said polarization-separation diffraction grating is planar and has lines that are rectilinear and parallel to each other.

3. The spectrometer according to claim 2, wherein said planar optical-reflection surface is parallel to said lines of the polarization-separation diffraction grating, so that said first diffracted light beam and said second diffracted light beam are focused, for each wavelength of said plurality of wavelengths, by said focusing system to a same focusing point of said focusing surface, said focusing points being separated on said focusing surface according to said plurality of wavelengths.

4. The spectrometer according to claim 2, wherein said planar optical-reflection surface forms with said lines of the polarization-separation diffraction grating an angle comprised between 0° and 90°, so that said first diffracted light beam and said second diffracted light beam are focussed, for each wavelength of said plurality of wavelengths, by said focusing means to two distinct focusing points of said focusing surface, said two distinct focusing points being separated on said focusing surface.

5. The spectrometer according to claim 2, further comprising an exit slit, fixed or mobile, arranged on said focusing surface and configured to let through said diffracted light beams recombined by said focusing system on said focusing surface.

6. The spectrometer (200) according to claim 2, further comprising a detection arranged system disposed on said focusing surface and configured to deliver, for each wavelength of said plurality of wavelengths, a signal relating to the sum of the light intensity diffracted at said wavelength in the diffraction order +1 and the light intensity diffracted at said wavelength in the diffraction order −1.

7. The spectrometer according to claim 1, further comprising an exit slit, fixed or mobile, arranged on said focusing surface and configured to let through said diffracted light beams recombined by said focusing system on said focusing surface.

8. The spectrometer according to claim 1, further comprising a detection system disposed on said focusing surface and configured to deliver, for each wavelength of said plurality of wavelengths, a signal relating to the sum of the light intensity diffracted at said wavelength in the diffraction order +1 and the light intensity diffracted at said wavelength in the diffraction order −1.

9. The spectrometer according to claim 8, wherein said optical recombination system includes a planar mirror configured to reflect, for each wavelength of said plurality of wavelengths, said second diffracted light beam in a direction parallel to said first diffracted light beam, and said detector system include a multi-channel detector.

10. The spectrometer according to claim 8, wherein said optical recombination system includes a planar mirror configured to reflect, for each wavelength of said plurality of wavelengths, said second diffracted light beam in a direction parallel to said first diffracted light beam, and said detector system includes a mobile slit and a single-channel detector.

11. The spectrometer according to claim 1, wherein said optical recombination system includes a planar mirror configured to reflect, for each wavelength of said plurality of wavelengths, said second diffracted light beam in a direction parallel to said first diffracted light beam.

12. The spectrometer according to claim 1, wherein said optical recombination system includes a prism comprising a base, an entrance face, and an exit face inclined with respect to the entrance face, said entrance face and said exit face refracting, for each wavelength of said plurality of wavelengths, said first diffracted light beam and said second diffracted light beam, said second diffracted light beam being deviated, for each wavelength of said plurality of wavelengths, by reflection on said base of the prism between said entrance face and said exit face.

13. The spectrometer according to claim 11, further comprising:
an exit slit, fixed or mobile, arranged on said focusing surface and configured to let through said diffracted light beams recombined by said focusing system on said focusing surface;
a fluorescence cell and a measurement system said fluorescence cell being arranged downstream of said exit slit to be illuminated by said recombined diffracted light beams and to emit a fluorescence signal, said measurement system being configured to measure the light intensity of said fluorescence signal.

14. The spectrometer according to claim 1, wherein said optical recombination system includes:
a quarter-wave retardation plate disposed at the exit of said polarization-separation diffraction grating, said quarter-wave retardation plate being configured to modify said first polarization state and said second polarization state to transform their orthogonal circular polarization states into linear polarization states that are orthogonal to each other,
a first mirror and a second mirror disposed parallel to each other to face each other and perpendicular to said polarization-separation diffraction grating, so that said first mirror, and said second mirror, respectively reflects, for each wavelength of said plurality of wavelengths, said first diffracted light beam and said second diffracted light beam, and
a polarization-recombining cube having a recombination interface that is placed between said first mirror and said second mirror, so that said first diffracted light beam reflected by said first mirror is incident on a first entrance face of said polarization-recombining cube and that said second diffracted light beam reflected by said second mirror is incident on a second entrance face of said polarization-recombining cube, one of said reflected diffracted light beams being reflected by said recombination interface and the other reflected diffracted light beam being transmitted by said recombination interface, said first diffracted light beam and said second diffracted light beam being parallel at the exit of said polarization-recombining cube.

15. The spectrometer according to claim 1, wherein said collimation system comprises an optical collimation system having a collimation numerical aperture, and
the focusing system comprises an optical focusing system having a focusing numerical aperture that is at least equal to the double of said collimation numerical aperture.

* * * * *